United States Patent [19]

Barratt

[11] 4,193,496
[45] Mar. 18, 1980

[54] DISPOSABLE RECEIVER

[76] Inventor: Don C. Barratt, 4704 Butterfield Dr., Arlington, Tex. 76017

[21] Appl. No.: 952,968

[22] Filed: Oct. 20, 1978

Related U.S. Application Data

[63] Continuation-in-part of Ser. No. 928,251, Jul. 26, 1978, Pat. No. 4,167,230.

[51] Int. Cl.² ............................................. A61L 17/02
[52] U.S. Cl. .................... 206/380; 206/63.3; 206/382; 220/306; 220/307; 229/2.5 R; 229/43
[58] Field of Search ............... 206/380, 382, 470, 438, 206/63.3; 229/2.5 R, 44 R, 43; 220/306, 307

[56] References Cited

U.S. PATENT DOCUMENTS

| 3,084,842 | 4/1963 | Beech | 229/2.5 |
|---|---|---|---|
| 3,111,220 | 11/1963 | Bostrom | 206/470 |
| 3,164,478 | 1/1965 | Bostrom | 229/2.5 |
| 3,552,595 | 1/1971 | Gerner et al. | 229/2.5 |
| 3,723,061 | 3/1973 | Stahl | 206/370 |
| 4,008,802 | 2/1977 | Freitag | 206/382 |

Primary Examiner—William T. Dixson, Jr.
Attorney, Agent, or Firm—James F. Cottone

[57] ABSTRACT

An improved disposable receiver, formed by foldably nesting a shaped cover element into a correspondingly shaped tray element, for securely encasing sharp disposable surgical implements features a combination of reopenable retaining and locking means for retaining the receiver in the closed, nested position. In a preferred embodiment, the disposable receiver may be formed of transparent plastic material into symmetrical tray and cover portions separated by an integrally formed flexible hinge, and a number of integrally formed pressure fit snap locks are arrayed around the periphery of the receiver to provide readily reopenable closure retaining means. Additionally, the tray and cover portions are slightly pyramidally shaped to produce a receiver of high rigidity when in the closed, nested position.

21 Claims, 8 Drawing Figures

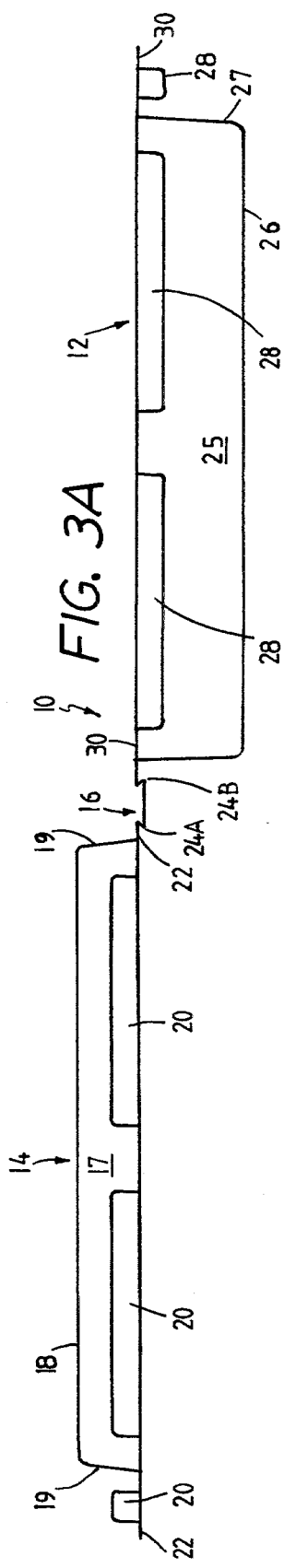
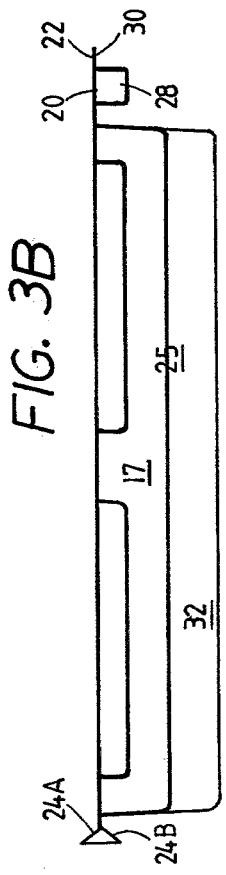
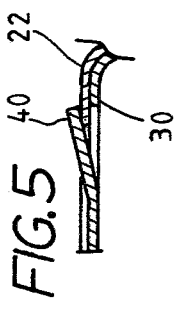
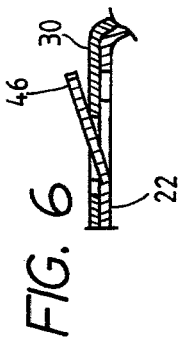
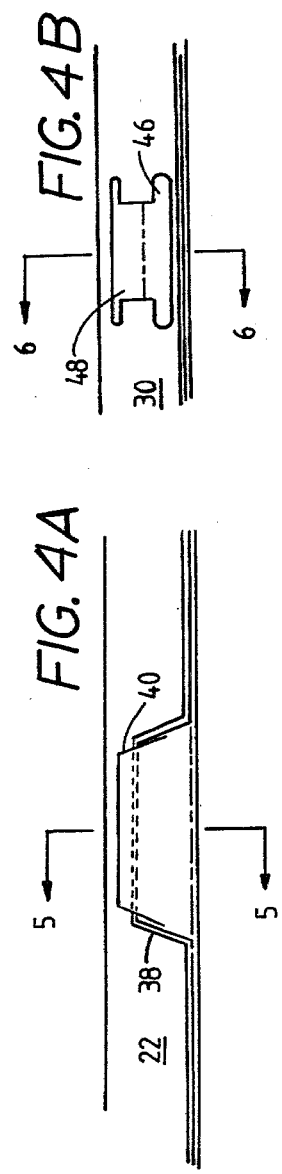

DISPOSABLE RECEIVER

The present application is a continuation-in-part of a copending application entitled "Disposable Receiver", Ser. No. 928,251, filed July 26, 1978 U.S. Pat. No. 4,167,230.

BACKGROUND OF THE INVENTION

1. Field of the Invention

The present invention relates to the field of disposable containers, and more specifically to a container having unique reopenable closure retaining and locking means for use as a receiver of used sharp surgical implements prior to their disposal.

2. Description of the Prior Art

During virtually every surgical procedure, sharp implements, such as suture needles, scalpel blades and hypodermic needles are utilized and, following the surgical procedure, must be discarded in a safe manner. If the safety aspect of the discarding of such implements is disregarded, injury and infection of the operating room and other hospital personnel may result. In order to combat this problem, many products have recently been introduced to the marketplace and many other products have been proposed in various patents.

Another serious problem attendant to the use of such sharp implements (hereinafter referred to alternately as "sharps") during surgery is the necessity of providing an accurate system for determining how many such implements were used and to also insure that all such implements have been accounted for following the surgical procedure. Various sharps count systems and devices also have been proposed to alleviate this problem.

A receiver for surgical implements utilizing a plurality of magnets which are secured to the surface of a foldable foamed elastomeric backing sheet is proposed in U.S. Pat. No. 3,727,658 to Eldridge, Jr. Similar systems employing an adhesive coating on a foldable pad are described and illustrated in U.S. Pat. No. 3,944,069, also to Eldridge, Jr., and U.S. Pat. No. 4,076,882 to Fenster. Another system similar to the systems described in the three previously cited patents, but also providing for a method for maintaining an accurate count of the number of sharp implements utilized during the surgical procedure, is illustrated and described in U.S. Pat. No. 4,008,802 to Freitag.

In another U.S. Pat. No. 4,013,109, to Sandel, a disposable container for surgical instruments is described which embodies a non-deformable casing which has magnetic sheets covering the entire interior surfaces of both the lower and upper portions of the case.

All of the disposable receivers described in the above-cited patents suffer from a number of disadvantages and notably among the disadvantages is the inability of the operating room personnel to make a visual inspection of the receiver or container after it has been readied for disposal. For example, although U.S. Pat. No. 4,008,802 discloses a system for maintaining a count of the used sharp implements, this count cannot be verified after the pad has been folded upon itself and adhesively secured together without again opening the pad by overcoming the force of the adhesive attachment.

Briefly, prior art disposable receiver disadvantages are that most can be opened accidentally as with magnetic or hook and loop (Velcro) closures. Others are rendered useless when reopened as in adhesive closures; rigid plastic receivers fracture easily and the ball or pin snap closures fail; most allow lateral side exposure of unsecured sharps; each instance does not allow for safe handling, safe disposal or reopening for accountability of used sharps.

Furthermore, the disposable receivers described and illustrated in the first four patents cited above are constructed so that the sharps may be exposed at the lateral edges of the receivers when they are in a folded, disposable condition. This is undesirable in that it is possible that the implements can be loosened from their attachment to the devices and either be totally dislodged from the devices or placed in an unsafe position thereby creating a potential hazard. This condition is sought to be eliminated by the relatively rigid structure proposed in U.S. Pat. No. 4,013,109. However, this container does not provide a count system for the sharp implements or does it supply a means for visual inspection of the implements after the container has been closed and readied for disposal.

A need exists for a system for the safe disposal of sharps which eliminates the various disadvantages which have been experienced with previously proposed devices.

SUMMARY OF THE INVENTION

It is therefore a primary object of the instant invention to provide an improved disposable receiver for securely encasing and disposing of sharps during and following a surgical procedure; and one which overcomes the disadvantages of the prior art devices.

The invention described in the aforementioned copending application provides a number of unique features which the present invention compliments and provides improvements on. The improvements include the use of a combination of closure retaining and locking means which are integrally formed into the improved disposable receiver elements themselves, thereby eliminating the use of adhesive, hook and loop (Velcro) and magnetic closing means. Also, the tray and cover elements of the improved disposable receiver has been specially shaped thereby imparting a surprising rigidity to the device and providing benefits both in use and during manufacturing.

A further object of this invention is to provide an improved disposable receiver which has integrally formed means for retaining the receiver in the closed position whereby the receiver may be reopened, if required, without undue stress or damage to the receiver and without undue or complex manipulation by the user.

Another object of this invention is to provide an improved disposable receiver having a combination of different restraining and locking means all utilizing simple friction-type forces, each of which gives a hierarchy of retention, and all of which are readily reopenable as above.

Another object of this invention is to provide an improved disposable receiver comprised of tray and cover elements which are configured to nest into the closed position, wherein a slightly pyramid-like shape is formed into the elements thereby giving a high degree of rigidity to the receiver. This increased rigidity allows for ease of handling in use, greater safety during disposal, and provides economies in manufacture.

BRIEF DESCRIPTION OF THE DRAWINGS

Additional objects and advantages of the invention will become apparent to those skilled in the art as the description proceeds with reference to the accompanying drawings wherein:

FIGS. 3A and 3B are side views of the improved receiver showing, respectively, the device in the open and closed positions, and unmated and mated pressure fit snap locks;

FIGS. 4A and 4B are fragmentary views showing details respectively of the finger notch/locking slot means and the tab/slot locking means; and FIGS. 5 and 6 are cross-sectional views associated with FIGS. 4A and 4B, respectively.

DETAILED DESCRIPTION OF THE PREFERRED EMBODIMENTS

Figure 1:
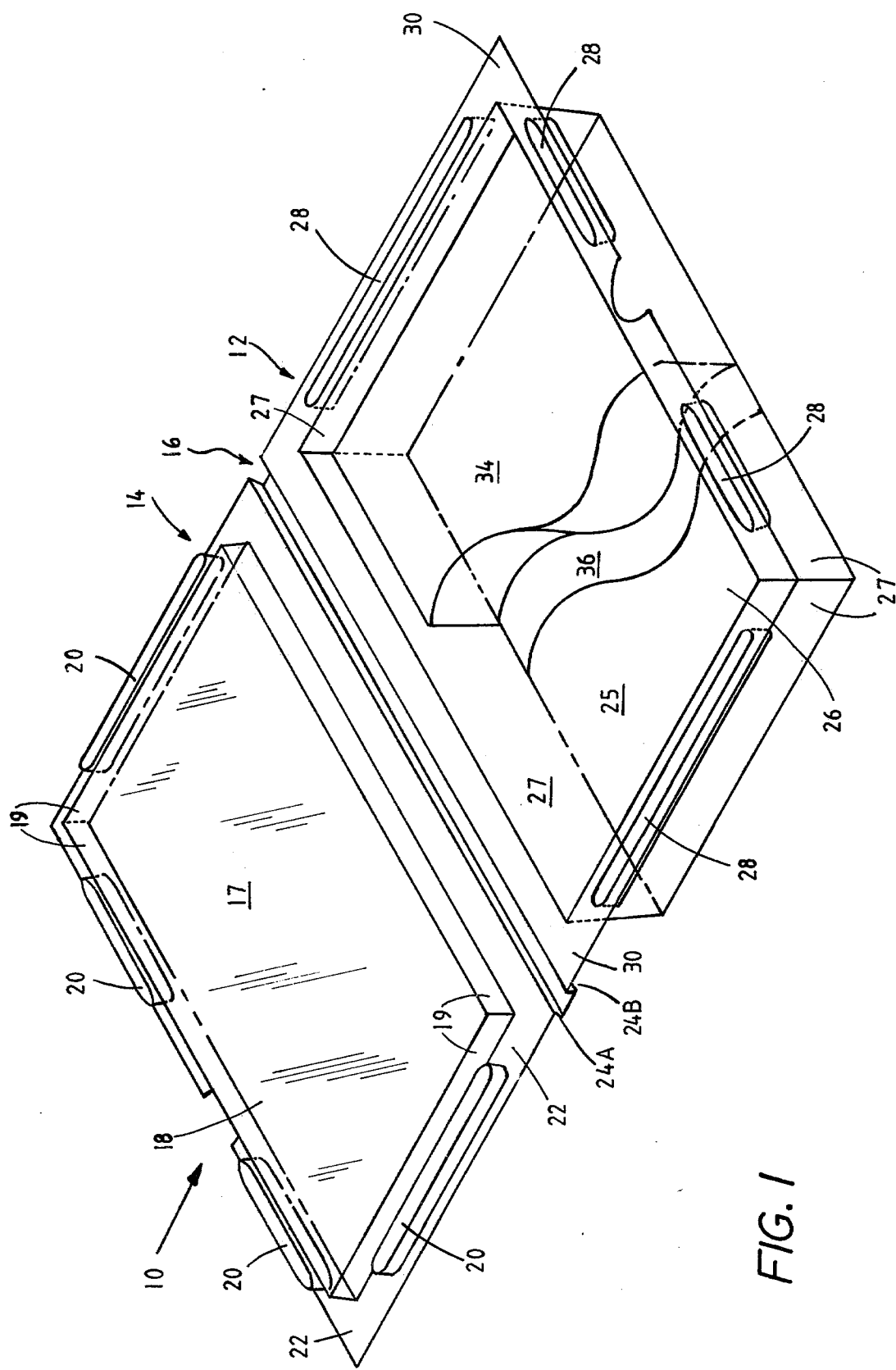
FIG. 1 is a perspective view of the improved disposable receiver according to the present invention.

Referring now to FIG. 1, there is shown a perspective view of the Improved Disposable Receiver according to the present invention. The receiver is shown in its open position generally at 10 as being comprised of a bottom tray 12 and a top cover 14, which are interconnected by means of a flexible hinge region 16. The top cover 14 may be shaped by a thermal forming, or similar, process so as to produce a large cavity-like volume 17 centrally disposed therein having a bottom wall 18 and side walls 19; and is similarly shaped to produce a plurality of smaller elongated cavity-like volumes 20 arrayed along three of the four sides of a flat peripheral flange 22 which extends outwardly around the lower (as depicted) periphery of the volume 17. The bottom tray 12 may be similarly formed to have a large cavity-like volume 25 centrally disposed therein having a bottom wall 26 and side walls 27; and further to have a plurality of smaller elongated cavity-like volumes 28 arrayed along three of the four sides of a flat peripheral flange 30 which extends outwardly around the upper periphery of the volume 17. When the receiver is in the open position, the flanges 22 and 30 are substantially coplanar. The side walls 19 and 27 of volumes 17 and 25 are angled slightly from the vertical to impart additional rigidity to the tray 12 and the cover 14. This feature is not readily apparent in FIG. 1 but is more clearly seen in FIGS. 3A and 3B. Brief reference to FIG. 3A shows that both of the volumes 17 and 25 may be characterized as being short truncated pyramidal-like sections. Also, the volumes 17 and 25 are dimensioned such that when they are nested—with cover 14 inserted into tray 12—a slight interference fit obtains which maintains the elements in the closed (alternately hereinafter referred to as the nested) position.

In the illustrative embodiment shown, the improved receiver is rectangular in overall shape and may be formed from a moldable, yieldable, transparent or opaque sheet of plastic or resin thereby providing a device of unitary construction. While the description herein is largely in terms of this rectangular configuration, the receiver obviously may take on the range of overall shapes, such as oval, polygonal, and the like.

The plurality of small elongated volumes 20 are positioned and configured so as to mate directly with the corresponding ones of the plurality of elongated volumes 28 when the top cover 14 and bottom tray 12 portions of the receiver are nested in the closed position. Referring again briefly to FIG. 3A which shows the disposable receiver in its open position, it will be noted that the volume 17 formed in the top cover 14 is disposed above a horizontal plane containing the flanges 22 and 30, and that the volume 25 formed in the bottom tray 12 is disposed below the plane containing the flanges. Further, the side walls 19 are shorter in height than the side walls 27. This height difference (not shown to scale) results in the formation of a sharps containment volume 32 (volume 25 of the bottom tray 12 minus the volume 17 of the top cover 14), as seen best in FIG. 3B, which shows the disposable receiver in its closed, nested position.

Shown in FIG. 1 (but for clarity omitted in FIGS. 3A and 3B) is a layer of resilient material 34 shaped and positioned so as to fit securely within the volume 25 of the bottom tray 12. The resilient material 34 may be comprised of polyurethene foam, or the like, and may be secured to the bottom wall 26 of the volume 25 by means of a thin coating 36 of tacky or adhesive composition. The resilient material 34 (also not to scale) and the thin coating 36 are shown in fragmented form for clarity of exposition, but extend to cover substantially the entire bottom wall 26 of the volume 25. It should be noted that the thickness of the resilient material 34 is less than the depth of the volume 25. Therefore, when the top cover 14 is foldably mated with the bottom tray 12, the resulting sharps containment volume 32 is substantially filled by the resilient material 34, thereby aiding in the secure retention of the disposed sharps by compressional forces. While the basic illustrative embodiment contemplates the use of plain uncoated materials for the resilient material 34, alternate embodiments will be described hereinbelow wherein the resilient material 34 may be fitted with auxiliary layers (magnetic, adhesive, or the like) to enhance the retention of the sharps.

Figure 2:
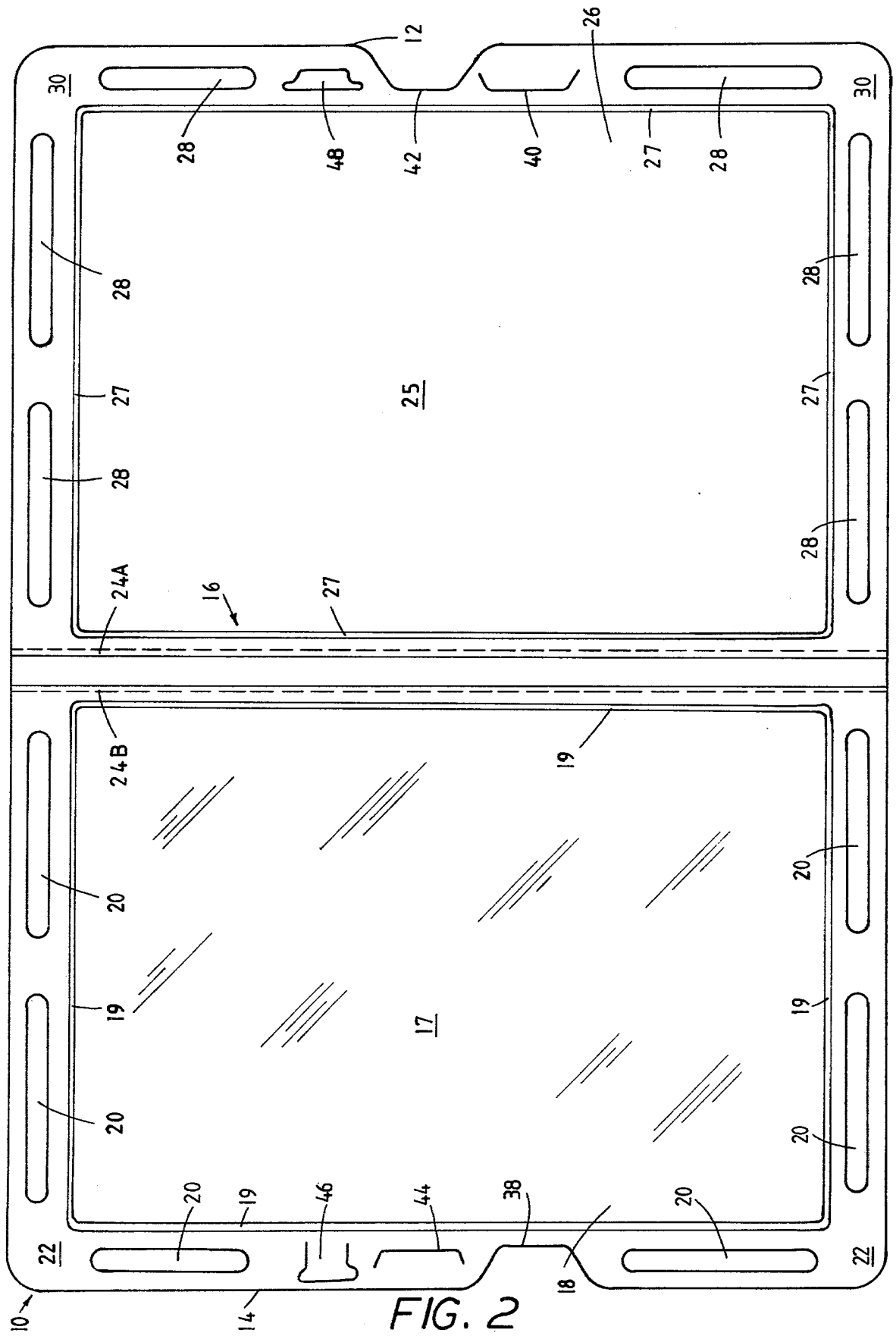
FIG. 2 is a top view of the improved disposable receiver.

Referring now to FIG. 2, there is shown a top view of the Improved Disposable Receiver 10 in its opened position. As in FIG. 1, the device as shown is comprised primarily of a top cover 14 and a bottom tray 12 separated by a flexible hinge region 16. The plurality of elongated volumes 20 disposed along three of the four sides of the top cover 14 are clearly shown as corresponding to a like plurality of volumes 28 disposed along three of the four sides of the bottom tray 12. FIG. 2 shows the volumes 20 and 28 as being comprised of six individual elements, while FIG. 1 optionally shows these as being comprised of four individual elements. The exact number of elements is not significant in itself as the number and placement of the elements depends primarily on the overall size and shape of the reciever. Functionally, these elongated volumes (hereinafter referred to as pressure-fit snap locks) are used to retain the disposable receiver firmly in the closed (or nested) position while permitting easy re-opening of the receiver as required without incurring damage to the elements allowing the sharps to be covered periodically during the surgical procedure for added safety.

Two additional locking means are employed to retain the receiver in the closed position. The first of these is a pair of finger notches/locking slots designated as a notch 38 in the top cover 14 which cooperates with a U-shaped slot 40 in the bottom tray 12; and a notch 42 in the bottom tray 12 which cooperates with a U-shaped slot 44 in the top cover 14. The pair of finger notches/locking slots are positioned along the longer dimensions of the peripheral flanges 22 and 30. The second of these locking means is a positive locking tab 46 suitably positioned along the peripheral flange 22, which cooperates with a receiving aperture 48 suitably positioned along the peripheral flange 30.

Referring now briefly to FIGS. 4A and 4B, there are shown fragmentary top views of these two locking means in their closed positions. FIG. 4A shows an engaged finger notch/locking slot arrangement, and FIG. 5 shows a vertical cross section through the corresponding interlocking layers. FIG. 4B shows an engaged locking tab/receiving aperture combination, and FIG. 6 shows the corresponding cross-sectional view of the mating parts.

While all three closure retaining means function to retain the receiver in the closed position, they are optimized to provide various levels of retention. The pressure fit snap locks (elements 20 and 28) may be used for short term holding, such as when the receiver is being periodically opened and closed. These snap locks also provide positive acting means for closing up the sides of the receiver thereby precluding the encased sharps from accidentially protruding from the receiver sides. The positive locking tab/receiving aperture (elements 46 and 48) are used for the final locking function just prior to the disposal of the receiver. The finger notch/locking slot (elements 38 and 40) provide an intermediate level of receiver locking.

Therefore it is seen that the present invention provides a disposable receiver having a combination of means for securely and positively locking the receiver at various stages in its use, but inherent in each of the retaining or locking means is the capability of reopening the receiver if required. Thus, for example, the pressure fit snap locks, or the finger notch/slot elements, may be used to close the receiver during a surgical procedure, and the positive acting locking tab/aperture slot may be used as a final step when the receiver containing the sharps is to be disposed of. The action of the locking tab/aperture slot is such that an overt, conscious manipulation is required thereby precluding accidental opening. However, should a last minute inventory of the sharps be required, any or all of the three locking/retention means may be manipulated to reopen the receiver without damage to the individual elements. Further, each of the locking/retention means may be actuated a number of times without damage to any of the elements while requiring only the usual amount of care during operation.

In use, the receiver is opened and the sharps to be disposed are placed on the resilient material 34 in accordance with the customary practice of the users. As an aid in retaining the sharps, the material 34 may be coated with a layer of adhesive, or an array of magnetic strips, or the like. Also, the material 34 may be formed with a series of raised ridges through which needles and sutures, etc., may be passed for retention. Upon being closed, the tray 12 and cover 14 nest together thereby encasing the sharps and the resilient material 34 as well as the adhesive or magnetic (or other) means to assure that the sharps are restrained from moving. Thereafter, the various retaining/locking means are actuated as often as required, and subsequently the entire receiver is disposed of.

Although the invention has been described in terms of selected preferred embodiments, the invention should not be deemed limited thereto, since other embodiments and modifications will readily occur to one skilled in the art. It is therefore to be understood that the appended claims are intended to cover all such modifications as fall within the true spirit and scope of the invention.

What is claimed is:

1. A reopenable disposable receiver for securely encasing sharps for disposal, comprising:
   (a) a bottom tray having a bottom wall with side walls extending upwardly from said bottom wall and a flange extending outwardly around the upper periphery of said side walls;
   (b) a top cover having a bottom wall with side walls extending upwardly from said bottom wall and a flange extending outwardly around the upper periphery of said side walls;
   (c) wherein said tray is hingedly connected to said cover such that said cover may be placed over and nested into said tray with the bottom wall of said cover in close proximity to the bottom wall of said tray to securely encase sharps therebetween; and
   (d) a plurality of retaining means types integrally formed into said flanges as indentations of opposite cooperating geometries for retaining said tray and said cover in the nested position via a hierarchy of retaining means.

2. The reopenable disposable receiver of claim 1 further comprising receiving means on said tray bottom wall for receiving said sharps.

3. The reopenable disposable receiver of claim 2 wherein the side walls of said cover are shorter than the side walls of said tray to provide a volume between the respective bottom walls to accommodate said receiving means and said sharps.

4. The reopenable disposable receiver of claim 3 wherein said receiving means is comprised of a layer of resilient material which substantially fills the volume formed between the tray bottom wall and the cover bottom wall thereby securely holding the encased sharps by compressional forces.

5. The reopenable disposable receiver of claim 4 wherein said retaining means comprises at least one friction fit snap lock having an elongated embossed first element formed into said tray flange with side walls extending downwardly from said flange, and an elongated embossed second element formed into said cover flange with side walls extending downwardly from said flange, for frictionally retaining said tray and said cover in the nested position upon mating engagement of the first and second elements.

6. The reopenable disposable receiver of claim 5 wherein said receiver is generally rectangular in shape when in the closed, nested position and said hinged connection of said tray and said cover is accomplished along a longer side of the respective flanges extending around the peripheries of said tray and said cover.

7. The reopenable disposable receiver of claim 6 having at least two of said snap lock retaining means disposed along the flanges of said receiver.

8. The reopenable disposable receiver of claim 3 wherein the side walls of said tray and said cover are angled such that the volume defined by each of the bottom walls and its respective side walls takes on the shape of a truncated pyramid-like section with the interior angles between each bottom wall and its adjacent side walls being an obtuse angle, thereby imparting increased rigidity to said receiver.

9. In a receiver for securely encasing pointed disposable surgical implements for disposal, having: a tray with a bottom wall, side walls extending upwardly from said bottom wall and a flange extending outwardly from the upper periphery of said side walls; means on said bottom wall for receiving said implements; and a cover with a bottom wall, side walls extending upwardly from said bottom wall and a flange extending outwardly from the upper periphery of said side walls; wherein said tray flange along one side wall is hingedly connected to said cover flange along one side wall so that said cover and said tray may be folded from a substantially coplanar position to a closed, nested position with the bottom wall of said cover in close proximity to the bottom wall of said tray to securely encase implements therebetween, the improvements comprising: forming a plurality of frictional retaining means types into said tray flange and said cover flange as indentations of cooperating opposite geometries to reopenably retain said receiver in the closed, nested position via a hierarchy of retaining means.

10. In the receiver of claim 9, the further improvement comprising: forming the side walls of said tray and said cover at an angle such that the volume defined by each of the bottom walls and its respective side walls takes on the shape of a truncated pyramid-like section with the interior angles between each bottom wall and its adjacent side walls being an obtuse angle thereby increasing the rigidity of said receiver.

11. In a receiver for securely encasing pointed disposable surgical implements for disposal, having: a tray with a bottom wall, side walls extending upwardly from said bottom wall and a flange extending outwardly from the upper periphery of said side walls; means on said bottom wall for receiving said implements; and a cover with a bottom wall, side walls extending upwardly from said bottom wall and a flange extending outwardly from the upper periphery of said side walls; wherein said tray flange along one side wall is hingedly connected to said cover flange along one side wall so that said cover and said tray may be folded from a substantially coplanar position to a closed, nested position with the bottom wall of said cover in close proximity to the bottom wall of said tray to securely encase implements therebetween, the improvements comprising: forming the side walls of said tray and said cover at an angle with their respective bottom walls such that the volume defined by each of the bottom walls and its respective side walls takes on the shape of a truncated pyramid-like section with the interior angles between each bottom wall and its adjacent side walls being an obtuse angle.

12. A reopenable disposable receiver for securely encasing sharps for disposal, comprising:
  (a) a bottom tray having a bottom wall with side walls extending upwardly from said bottom wall and a flange extending outwardly around the upper periphery of said side walls;
  (b) a top cover having a bottom wall with side walls extending downwardly from said bottom wall and a flange extending outwardly around the upper periphery of said side walls;
  (c) receiving means on said tray bottom wall for receiving said sharps comprising a resilient material and occupying substantially the entire enclosure;
  (d) wherein said bottom tray is hingedly connected to said top cover such that said cover may be folded from a substantially coplanar position to a closed, nested position with the bottom wall of said cover in close proximity to the bottom wall of said tray to securely encase sharps in an enclosure formed therebetween by compressional forces; and
  (e) a plurality of retaining means types integrally formed into said flanges as indentations of opposite cooperating geometries for retaining said tray and said cover in the nested position via a hierarchy of retaining means.

13. The reopenable disposable receiver of claim 12 wherein said retaining means comprises tab and aperture locking means having a suitably positioned tab element formed into said tray or cover flange and a correspondingly suitably positioned aperture element formed into said cover of tray flange for positive retention of said tray and cover in the nested, closed position upon mating engagement of said tab and aperture elements.

14. The reopenable disposable receiver of claim 12 wherein said retaining means comprises indented notch and u-shaped slot retaining means having a suitably positioned indented notch formed into said tray or cover flange and a correspondingly suitably positioned u-shaped notch formed into said cover or tray flange for interference fit retention of said tray and said cover in the nested, closed position upon mating engagement of said indented notch and u-shaped slot elements.

15. The reopenable disposable receiver of claim 12 wherein said retaining means comprises at least one friction fit snap lock having an elongated embossed first element formed into said tray flange with side walls extending downwardly from said flange, and an elongated embossed second element formed into said cover flange with side walls extending downwardly from said flange, for interference fit retention of said tray and said cover in the nested position upon mating engagement of said first and second elements.

16. The reopenable disposable receiver of claim 12 wherein said retaining means comprises in combination:
  (a) tab and aperture locking means formed into said tray and cover flanges for positive retention of said receiver in the closed position;
  (b) indented notch and u-shaped slot retaining means formed into said tray and cover flanges for interlocking fit retention of said receiver in the closed position; and
  (c) friction fit snap lock retaining means formed into said tray and cover flanges for interference fit retention of said receiver in the closed position.

17. The reopenable disposable receiver of claim 4 or claim 12 wherein said receiving means further comprises magnetic means attached thereto for improved retention of said sharps when the receiver is in either the opened or nested, closed position.

18. The reopenable disposable receiver of claim 4 or claim 12 wherein said resilient receiving means further comprises adhesive means disposed thereon for improved retention of said sharps when the receiver is in either the opened or nested, closed position.

19. The reopenable disposable receiver of claim 7 or claim 8 or claim 12 wherein said tray and said cover and said hinged connection are integrally formed from a single sheet of material thereby producing a receiver of unitary construction.

20. The reopenable disposable receiver of claim 7 or claim 8 or claim 12 wherein said material is transparent to allow inspection of the contents of the receiver when in the nested, closed position.

21. The reopenable disposable receiver of claim 7 or claim 8 or claim 12 wherein said material is thermoformable to allow thermal forming of said side walls, flanges, bottom walls and retaining means in said tray and said cover from single sheet of material.

* * * * *